United States Patent [19]

Pfeiffer et al.

[11] 4,026,154

[45] May 31, 1977

[54] SAMPLE TAKING APPARATUS

[75] Inventors: Hartmut Pfeiffer, Hesse; Manfred Hilbig; Wolfgang Krella, both of Neubeckum, all of Germany

[73] Assignee: Polysius AG, Neubeckum, Germany

[22] Filed: Apr. 10, 1975

[21] Appl. No.: 566,783

[30] Foreign Application Priority Data

Apr. 23, 1974   Germany .................... 7414019[U]

[52] U.S. Cl. .............................. 73/423 R; 250/357
[51] Int. Cl.² .................... G01F 23/00; G01N 1/20
[58] Field of Search ......... 73/421 R, 423 R, 290 R; 193/31 R, 31 A; 198/45; 250/357

[56] References Cited

UNITED STATES PATENTS

| 674,095 | 5/1901 | Overstrom ...................... 73/423 R |
| 3,175,402 | 3/1965 | Higami et al. .................. 73/423 R |

*Primary Examiner*—Richard C. Queisser
*Assistant Examiner*—Daniel M. Yasich
*Attorney, Agent, or Firm*—Learman & McCulloch

[57] ABSTRACT

Apparatus for taking samples from a stream of material discharged along a path from a conveyor comprises a gate movable between either one of two different positions in one of which the gate lies in the path of the stream of material and in the other of which the gate is clear of the path. Depending upon the position of the gate, the material is discharged to one of two different receivers.

5 Claims, 3 Drawing Figures

SAMPLE TAKING APPARATUS

This invention relates to apparatus for taking samples from a stream of granular or small-sized material being discharged along a path from a conveyor member, the apparatus including a reciprocating sample-taking element for extracting a portion of the material, together with means for receiving and removing the extracted sample of material.

It is in many cases necessary for the granular or small-sized material (for instant broken-up raw material consisting of stones, earth or the like) to have its condition continuously monitored while being fed to processing plant. For this reason samples must be taken regularly at periodic time intervals.

In a known sample-taking device, disposed for instance at the discharge point of a conveyor belt, there is provided a sample-taking chute which can be moved to and fro with the aid of a carriage or the like in the direction of the width of the discharged stream of material, so that it takes to some extent a strip of the stream of discharge material from the actual discharge zone. This diverted sample of material is then received by a device which conveys it for instance to analyzing equipment or the like.

If raw material having greatly varying grain or piece size is moved on a conveyor belt, experience shows that greater or lesser shifts occur in the size distribution of the material, which makes the taking of a representative sample very difficult. Thus when the sampling chute of the known device is moved across the width of the stream of material, this strip-wise sampling procedure from the stream of material can lead to considerable falsification. A further defect of this known construction lies in the complicated drive for the sample-taking chute, which must travel at least over the full width of the stream of material. In addition, because of the usually dusty surroundings, the drive elements are subject to heavy wear. A further problem lies in removing dust from the device, since complete encasement thereof presents difficulties.

The invention therefore has for its objective the avoidance of these difficulties of known constructions by providing a device of the type described which with a relatively simple design enables representative samples to be taken relatively quickly.

According to the invention this objective is achieved in that the sample-taking element comprises a flap or gate extending over the full width of the material, shielding the sample-receiving and removing device from the stream of material, and hingedly mounted at its one end so that is can pivot transversely to the width of the stream of discharged material.

When a sample has to be taken from a stream of material with the device provided by the invention, it is sufficient for the flap simply to tilt to and fro transversely to the width of the stream of material, so that is is not just a strip of the moving material which is deflected into the sample-receiving and removing device, as with the device mentioned above, but for a brief period the entire width of the stream of material. In this manner a truly representative sample of the discharged material can be taken in every instance.

Whereas the chute of the known device is moved in the direction of the width of the flow of material, the flap provided by the invention is moved transversely to the width, i.e., the flap need be moved only through the thickness of the stream of material, thereby requiring a relatively short traverse for the sample-taking element, and this helps to make sampling quicker.

The construction of the sample-taking element as a flap, which is its initial position seals off the sample-receiving and removing device from the stream of material, enables the constructional cost of the sample-taking device to be relatively low.

In accordance with the invention, for automatic sampling it is also desirable if the flap is connected with drive means which allow a relatively high pivoting speed. This drive means may with advantage comprise a pressure-medium driven, in particular a hydraulically driven cylinder and piston device, of relatively simple construction and applicable to standard commercial equipment.

In any case the sample-taking device in accordance with the invention can be installed without particular difficulty on or in a discharge chute or the like in a conveyor member; this installation also can be effected subsequently with conveyors which are already installed.

Some embodiments of the invention are described in more detail below with reference to the attached drawings, wherein.

Figure 1:
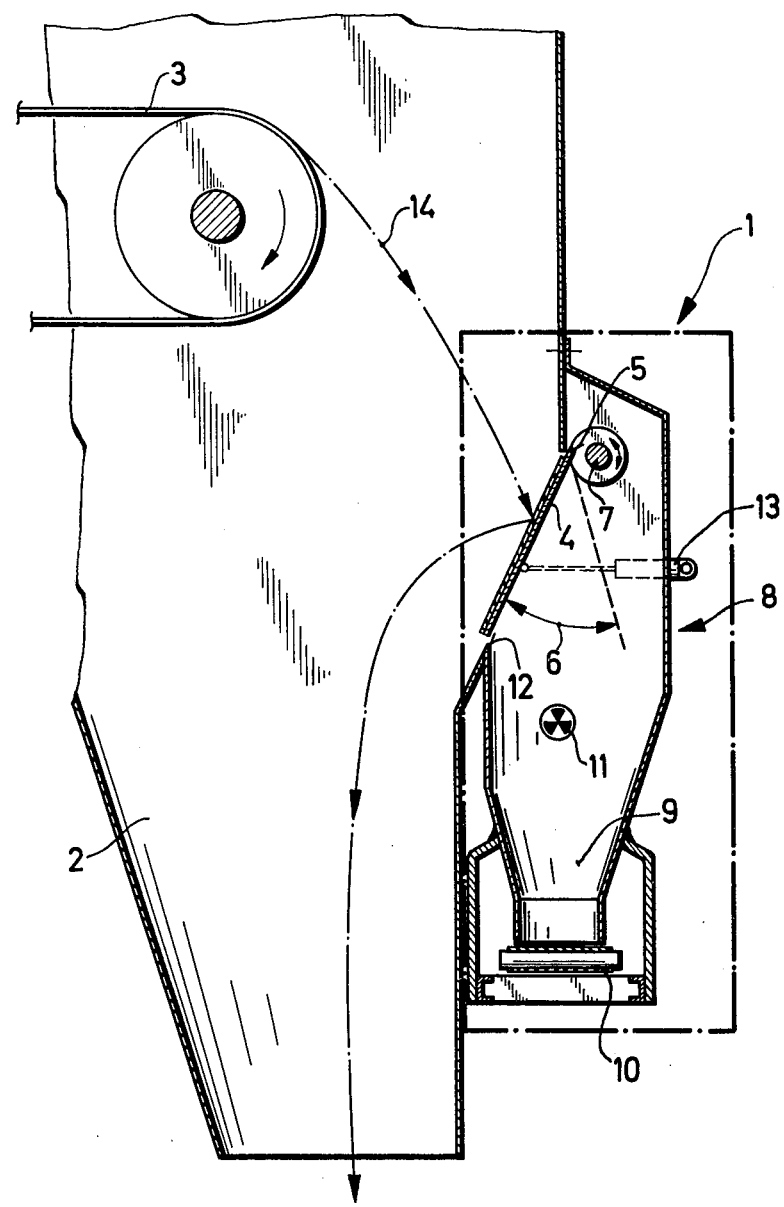
FIG. 1 is a schematic diagram of one embodiment.

In FIG. 1 the sample-taking device 1 is disposed generally at the front end of the discharge chute or receiver 2 into which material from a conveyor belt 3 may be discharged.

The sample-taking device 1, shown in cross-section, includes a gate or flap 4 hingedly mounted at its upper end 5 and adapted to pivot about the hinge axis 7 in the directions of the double arrow 6. The hinge axis 7 is at the upper end of a reception container or receiver 8 in the device 1, such container being funnel-shaped at its lower end and terminating above a conveyor member, comprising for instance a conveyor belt 10, which feeds the collected sample to analysis apparatus or the like. The reception container 8 and the conveyor member 10 together form the sample-receiving and removing means for the device 1.

The container 8 has a planar aperture 12 in communication with the receiver 2, the aperture normally being closed by the gate 4 which in its closed position as shown in full lines in FIG. 1 is inclined to the plane of the opening so that the lower, free end of the gate protrudes slightly into the receiver 2, thereby preventing inadvertent introduction of material into the container 8.

At a suitable position in the reception container there is also disposed a level monitoring member, in this case for instance comprising a gamma radiation device 11 such as that manufactured by Endrers & Hauser GmbH & Co., Maulberg Kreis Lorrach, Germany, and described in the manufacturer's technical bulletin No. 04.73.20E.

The device 1 is so disposed at the front of the discharge chute 2 that it extends over at least the full width of the stream of material, with the flap 4 also extending over the full stream width.

As may clearly be seen from FIG. 1, the flap 4 is disposed in the upper area of the reception container in such manner that in its initial (rest) position it blocks the aperture 12 in the reception container 8 which faces the discharge chute 2 and the stream of material.

As shown only in FIG. 1, the flap 4 is also engaged by a hydraulically operated cylinder and piston drive means 13 whereby the flap 4 can be pivoted at a relatively rapid rate into the reception container 8, so that the aperture 12 is then opened and the material discharged from the conveyor belt 3 can flow into the reception container 8 until the flap is pivoted back to its initial position, shown by a full line in FIG. 1.

It has also been found desirable for the flap 4 to be so disposed that the central or theoretical discharge line 14 of the path of the stream of material meets the side facing the stream of material somewhat above the centre of the flap 4 when said flap is in its initial position. This to a large extent ensures that during the sampling the stream of material reaches the reception container 8 not only over its full width but also over its full thickness. The precise dispostion of the device 1 and in particular of the flap 4 is thus in general based on the theoretical discharge line, also called the discharge parabola, of the path taken by material discharged from the conveyor belt 3, this curve 14 itself being largely dependent on the feed rate of the material from the conveyor belt 3 which is driven by conventional means, not shown.

The inclined setting or the angle of setting of the flap 4 in its initial position depends in general on the flow capacity of the material and on its erosion and cohesion properties.

When no sample of the material is being taken from the stream, the discharged material rebounds from the flap 4 and thus reaches the lower part of the discharge chute 2.

Figure 2:
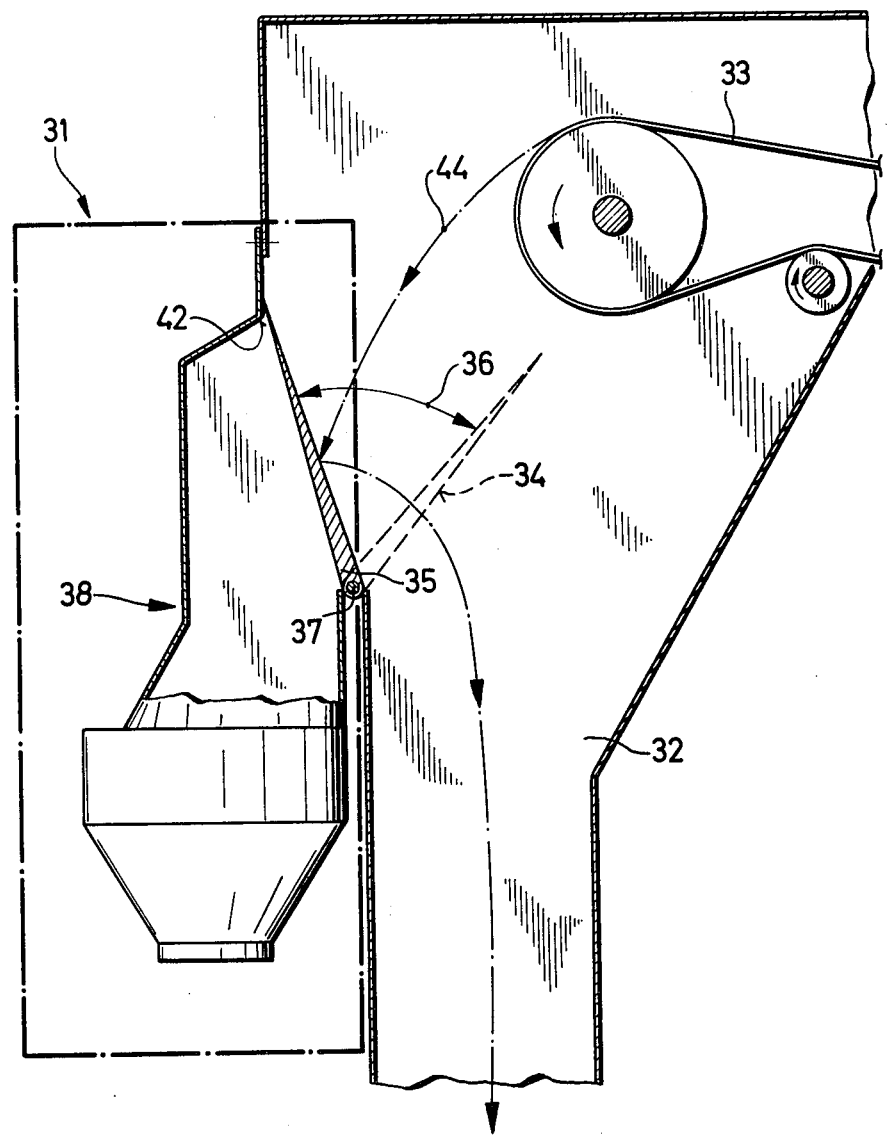
FIG. 2 is a similar diagram of a second embodiment.

FIG. 2 shows a somewhat different embodiment of a sample-taking device 31 in accordance with the invention. Again in this case the device 31 is applied to the front side of a discharge chute 32 provided at the end of a conveyor belt 33.

In this embodiment the flap 34 is hingedly mounted at its lower end 35 so that it can be pivoted about the axis 37 in the directions of the arrow 36 by cylinder and piston means like that discribed earlier. In its initial position the flap 34 faces the stream of material but has a greater length than that of the aperture 42 so as to be inclined to the plane of the aperture and rests on the wall of the container 38. The flap thus blocks the aperture 42 in the reception container 38 of a sample-receiving and removing means in the device 31. In other respects the flap 34, which extends over the full width of the stream of material, is disposed in similar manner to that shown in the FIG. 1 example in relation to the stream of material.

Whereas in the embodiment of FIG. 1 the sample-taking flap 4 is briefly pivoted into the receiving container 8, the flap 34 in the device 31 is tilted away from the receiving container 38, to the right in FIG. 2, which in any case ensures that in the course of sampling the entire stream of material passes into the reception container 38, which means that with the flap 34 outwardly tilted any fine sparyed grains are also conveyed into the container 38.

This second embodiment of the invention is not necessarily dependent on the theoretical discharge curve 44 of the stream of material. However, when the flap 34 is in its initial position the stream of material discharged from the conveyor belt 33 impinges on the flap 34 and is deflected therefrom into the lower part of the discharge chute 32. This embodiment makes particular allowance for the porperties of greasy, easy-flowing material.

Figure 3:
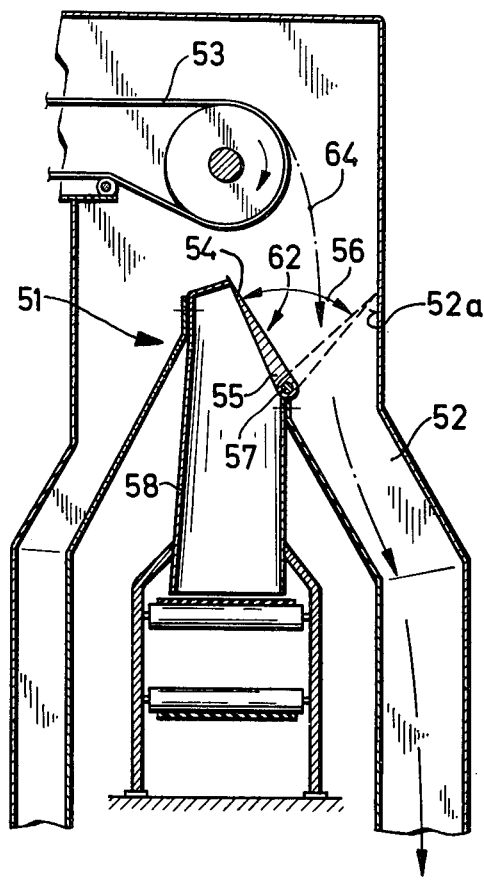
FIG. 3 is a similar diagram of a further embodiment.

The third embodiment of the invention shown in FIG. 3 is completely independent of the theoretical discharge curve 64 of the stream of material discharged from the conveyor 53. In this case the sample-taking device 51 is disposed below the discharge point or below the conveyor belt deflector roller, with the reception container 58 of the sample-receiving and removing device, as seen in the feed direction of the material being disposed at the rear side of the discharge chute 52, with the material receiving aperture 62 of the reception container 58 again directed towards the stream of discharged material.

The flap 54 which acts as a sample-taking element has a length greater than that of the aperture 62 and thus is inclined to the plane of the aperture, thereby enabling the free end of the flap to rest on the wall of the receiver 58 and block the aperture 62. The flap is hinged at its lower end 55 and is pivotable about the axis 57 in the directions of arrow 56 by means of the cylinder and piston assembly as before. In its initial position, shown in full lines in FIG. 3, the flap 54 is so disposed that the discharged stream of material hardly touches it, but drops directly into the discharge chute 52. When a sample is to be taken from the stream of material, the flap 54 is pivoted towards the outer face wall 52a of the discharge chute 52, i.e., to the right in the drawing (see the dotted line view of the flap in FIG. 3), so that during sampling the entire stream of material (in both width and depth) is again diverted into the reception container 58.

With all embodiments of the invention it is extremely desirable for the surfaces of the device which come into contact with the material to be provided with a wear-resistance coating as shown at C in FIG. 1; in many cases coatings may also be used which prevent the material coalescing.

What is claimed is:

1. Apparatus for taking samples from a continuous stream of material discharged from a conveyor along a downwardly curvilinear discharge path, said apparatus comprising a first material receiver and a second material receiver communicating with one another via a substantially planar aperture, one of said receivers constituting a sample receiver, said aperture having a width and a height at least as great as the width and thickness of said stream and being located at a level such that material tranversing said path normally would pass freely through said aperture; a planar gate having a free end; means mounting said gate at its opposite end for rocking movements between first and second positions, said gate having a width at least as great as the width of said stream and an area of such size relative to the area of said aperture as to be capable of blocking the latter whereby said material may impinge on said gate when the latter is in one of said positions; wear resistant means on that side of said gate on which said material may impinge; means in said sample receiver for sensing the level of material therein; conveyor means communicating with said sample receiver for conveying material therefrom; and means connected to said gate for rocking the latter between said positions, said gate when in one of said positions blocking said aperture with the free end of said gate on one side of the plane of said aperture and when in the other of said positions clearing said aperture and enabling said stream of material to pass through said aperture.

2. Apparatus according to claim 1 wherein said stream has a theoretical discharge curve, and wherein said mounting means mounts said gate at such level that its horizontal center line is at a level below said curve.

3. Apparatus according to claim 1 wherein said mounting means for said gate comprises a hinge and wherein said free end of said gate is at a level lower than that of said hinge.

4. Apparatus according to claim 1 wherein said mounting means for said gate comprises a hinge and wherein said free end of said gate is at a level above that of said hinge.

5. Apparatus according to claim 1 wherein the means for rocking said gate is pressure fluid operated.

* * * * *